United States Patent [19]

Watson et al.

[11] Patent Number: 4,888,043
[45] Date of Patent: Dec. 19, 1989

[54] HERBICIDAL AMINO-MESITYL CYCLOHEXANE-1,3-DIONE COMPOUNDS

[75] Inventors: Keith G. Watson; Craig G. Lovel, both of Melbourne, Australia

[73] Assignee: ICI Australia Limited, Melbourne, Australia

[21] Appl. No.: 876,748

[22] Filed: Jun. 20, 1986

[30] Foreign Application Priority Data

Jul. 12, 1985 [AU] Australia .............................. PH1448
Jul. 26, 1985 [AU] Australia .............................. PH1669

[51] Int. Cl.⁴ .................... A01N 43/40; A01N 37/22; A01N 37/24; C07D 333/24; C07C 131/08; C07C 119/06; C07C 131/04; C07C 131/10
[52] U.S. Cl. ......................................... 71/88; 71/90; 71/94; 71/98; 71/100; 71/103; 71/105; 71/106; 71/107; 71/111; 71/112; 71/115; 71/118; 71/122; 558/234; 560/27; 560/34; 560/35; 560/251; 562/437; 562/446; 564/29; 564/50; 564/82; 564/86; 564/90; 564/99; 564/212
[58] Field of Search ..................... 558/234; 560/27, 34, 560/35, 251, 513.5; 562/439, 440; 564/26, 50, 82, 86; 514/97, 99, 212; 71/118, 88, 90, 94, 95, 103, 105, 106, 111, 112, 115, 122, 107, 98, 118, 100

[56] References Cited

U.S. PATENT DOCUMENTS

| | | | |
|---|---|---|---|
| 3,950,420 | 4/1976 | Sawaki et al. | 564/256 X |
| 3,989,737 | 11/1976 | Sawaki et al. | 564/256 X |
| 4,440,556 | 4/1984 | Luo | 560/35 X |
| 4,482,740 | 11/1984 | Iwataki et al. | 564/99 |
| 4,504,305 | 3/1985 | Iwatake et al. | 564/84 X |
| 4,555,263 | 11/1985 | Serban et al. | 564/256 X |
| 4,604,128 | 8/1986 | Watson et al. | 564/86 X |
| 4,652,303 | 3/1987 | Watson et al. | 564/86 X |
| 4,666,510 | 5/1987 | Watson et al. | 564/86 X |
| 4,692,553 | 9/1987 | Keil, et al. | 564/185 |

FOREIGN PATENT DOCUMENTS

| | | | |
|---|---|---|---|
| 0085529 | 8/1983 | European Pat. Off. | 560/35 |
| 0136703 | 4/1985 | European Pat. Off. | 534/99 |
| 2116544 | 9/1983 | United Kingdom | 534/99 |

OTHER PUBLICATIONS

Garson et al., Chemical Abstracts, vol. 100, #6091k (1984).
Iwataki et al., I, Chemical Abstracts, vol. 99, #139389w (1983).
Iwataki et al., II, Chemical Abstracts, vol. 99, #212200j (1983).
Iwatake et al., III, Chemical Abstracts, vol. 82, #170218n (1975).
Warner et al., Chemical Abstracts, vol. 100, #102943k (1984).

Primary Examiner—Floyd D. Higel
Attorney, Agent, or Firm—Cushman, Darby & Cushman

[57] ABSTRACT

The invention concerns compounds of the formula I

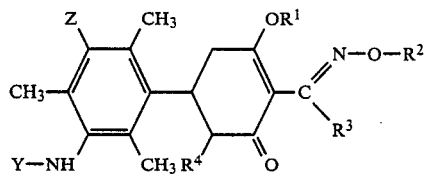

wherein:
  Z is selected from hydrogen, alkyl, alkanoyl, sulfamoyl, carboxy and trifluoroacetamido;
  Y is selected from various carboxy or thiocarboxy groups, haloalkanoyl, alkylsulfonyl and haloalkylsulfonyl;
  $R^1$ is selected from hydrogen, acyl and an inorganic or organic cation;
  $R^2$ is selected from alkyl, substituted alkyl, alkenyl, haloalkenyl and alkynyl;
  $R^3$ is selected from alkyl; and
  $R^4$ is selected from hydrogen, alkyl, and alkoxycarbonyl.

The compounds of the invention show herbicidal properties and plant growth regulating properties and in further embodiments and the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

10 Claims, No Drawings

HERBICIDAL AMINO-MESITYL CYCLOHEXANE-1,3-DIONE COMPOUNDS

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Patent No. 464 655 and its equivalents such as UK Patent No. 1 461 170 and U.S. Pat. No. 3,950,420.

A variety of herbicidal compounds containing 5-(substituted phenyl) cyclohexane-1,3-diones are described in the art. For example, French Patent No. 2,518,990, as well as the published British Patent application equivalent thereto, viz., No 2,116,544 describe various 5-(4-substituted phenyl) cyclohexane-1,3-diones and European Patent Application No. 085,529 describes various 5-(polysubstituted phenyl) cyclohexane-1,3-diones and their herbicidal properties.

It has now been found that a new group of cyclohexan-1,3-dione derivatives which have a 5-mesityl substituent which is in turn substituted with a particular kind of functionalized amino group, exhibit exceptionally high general grass-killing activity.

Accordingly the invention provides a compound of formula I

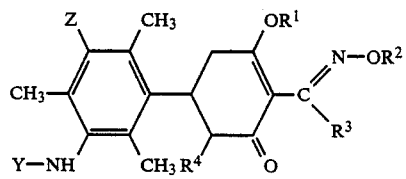

wherein
Y is selected from the group consisting of:
$C_1$ to $C_6$ alkylsulfonyl; $C_1$ to $C_6$ haloalkylsulfonyl; $C_2$ to $C_6$ haloalkanoyl; $R^5CO$ and $R^5CS$ wherein $R^5$ is selected from the group consisting of: hydroxy, $C_1$ to $C_6$ alkoxy, amino, $C_1$ to $C_6$ alkylamino and di($C_1$ to $C_6$ alkyl)amino;

Z is selected from the group consisting of hydrogen, halogen, $C_1$ to $C_4$ alkyl, $C_1$ to $C_4$ alkanoyl, sulfamoyl, $C_1$ to $C_4$ alkylsulfamoyl, di($C_1$ to $C_4$ alkyl)sulfamoyl, carboxy and trifluoroacetylamino;

$R^1$ is selected from the group consisting of: hydrogen; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_3$ to $C_6$ alkynyl; and substituted $C_1$ to $C_6$ alkyl wherein the alkyl group is substituted with a substituent selected from the group consisting of halogen, phenyl, and substituted phenyl wherein the benzene ring is substituted with from one to three substituents selected from the group consisting of halogen, and $C_1$ to $C_6$ alkyl;

$R^3$ is selected from the group consisting of: $C_1$ to $C_6$ alkyl; and $R^4$ is selected from the group consisting of: hydrogen; $C_1$ to $C_6$ alkyl; and ($C_1$ to $C_6$ alkoxy) carbonyl.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with rom one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^6R^7R^8R^9N^{\oplus}$ wherein $R^6$, $R^7$, $R^8$ and $R^9$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

The compounds of the invention may exist in two isomeric forms as shown below, wherein $\Phi$ represents the group

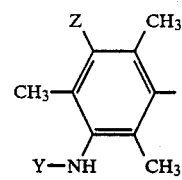

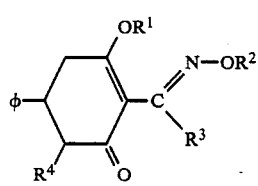

Ia

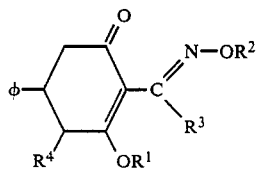

Id

It should be recognized that when $R^1$ is hydrogen the compounds of the invention may exist in any one of four tautomeric forms as shown below wherein φ represents the group

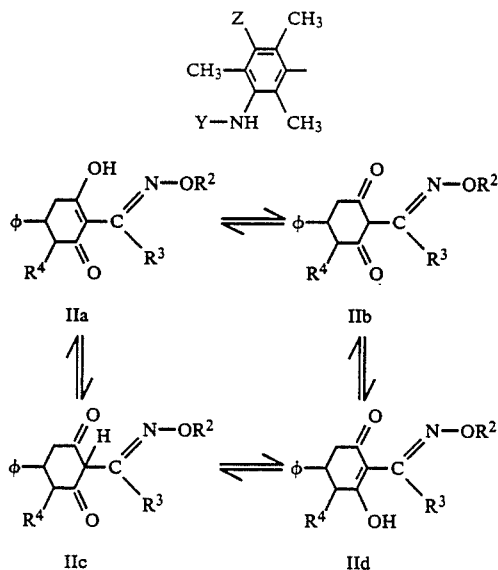

Preferred compounds of the invention include those compounds of formula I wherein:

the substituent Y is chosen from the group trifluoroacetyl; trifluoromethanesulfonyl; alkoxycarbonyl; carbamoyl and N-alkyl(thio)carbamoyl;

Z is selected from hydrogen, methyl, $C_2$ to $C_4$ alkanoyl, halogen, sulfamoyl, dimethylsulfamoyl and trifluoroacetylamino;

$R^1$ is selected from hydrogen, the alkali metal cations, $C_2$ to $C_6$ alkanoyl, benzoyl and substituted benzoyl wherein the benzoyl ring is substituted with from one to three substituents chosen from halogen, nitro and cyano;

$R^2$ is selected from the group consisting of $C_1$ to $C_4$ alkyl, $C_2$ to $C_4$ alkenyl, $C_3$ to $C_4$ alkynyl, $C_1$ to $C_4$ haloalkyl and $C_2$ to $C_4$ halo alkenyl;

$R^3$ is selected from $C_1$ to $C_6$ alkyl; and $R^4$ is hydrogen.

More preferred compounds of the invention include those compounds of formula I wherein:

Y is trifluoroacetyl, trifluoromethanesulfonyl or N-alkylcarbamoyl;

Z is selected from hydrogen, methyl or acetyl;

$R^1$ is selected from hydrogen and the alkali metal cations;

$R^2$ is selected from methyl, ethyl, n-propyl, allyl, propargyl and 3-chloroallyl;

$R^3$ is selected from methyl, ethyl and n-propyl;

$R^4$ is hydrogen.

Examples of compounds embraced by the invention include:

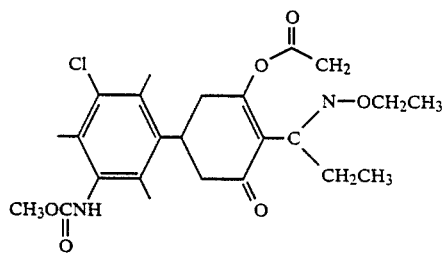

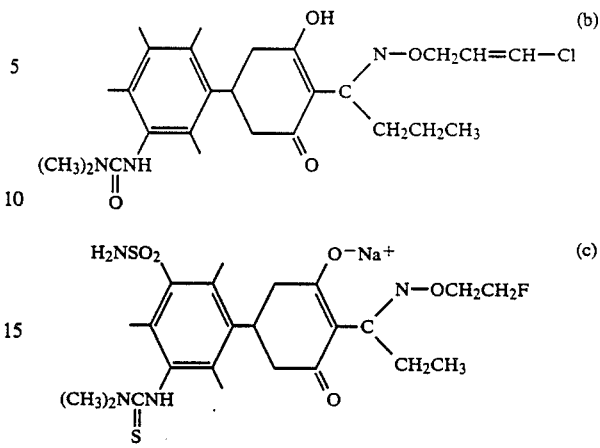

Specific examples of the compounds of the invention include those compounds detailed in Table 1 below.

TABLE 1

| Compound No | Y | Z |
|---|---|---|
| 1 | $SO_2CH_3$ | H |
| 2 | $CONH_2$ | H |
| 3 | $CSNHCH_2CH_3$ | H |
| 4 | $COCF_3$ | H |
| 5 | $COCF_3$ | $COCH_3$ |
| 6 | $COCCl_3$ | H |
| 7 | $CO(CF_2)_2CF_3$ | H |
| 8 | $CONH(CH_2)_2CH_3$ | H |
| 9 | $SO_2CF_3$ | H |
| 10 | $COCF_2CF_3$ | H |
| 11 | $CONHCH_3$ | H |

The compounds of the invention may be prepared by a variety of methods and in a further aspect the invention provides methods for the preparation of compounds of formula I.

Conveniently the preparation of the invention can be considered in four or five parts.

Part A involves the formation of a 5-arylcyclohexan-1,3-dione of formula IX. This reaction may be carried out in a two step process by:

(i) reacting, preferably in the presence of a base, an aldehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be isolated or hydrolysed directly, preferably in the presence of an acid, to give a 5-arylcyclohexan-1,3-dione of formula IX.

(ii) reacting, preferably in the presence of a base, an aldehyde derivative of formula V with an acetic acid ester of formula IVc to give a 2-arylalkenoate derivative of formula VIc which is in turn reacted, preferably in the presence of a base, with an acetoacetic acid ester derivative of formula VIIc to give an intermediate of formula VIIIa which may be isolated or hydrolysed directly, preferably in the presence of an acid, to give a 5-arylcyclohexan-1,3-dione of formula IX.

Part B involves the acylation of a compound of formula IX to give a 2-acylcyclohexane-1,3-dione derivative of formula Xa. Alternatively Part B involves the acylation of a compound of formula VIIIa or VIIIb to give a 2-acylcyclohexane-1,3-dione derivative of formula XIa or XIb respectively which may be hydrolysed, preferably in the presence of a base, to give a 2-acylcyclohexane-1,3-dione of formula Xa. The acylation reaction may be carried out by reacting a cyclohexane-1,3-dione derivative of formula VIII or IX with:

(i) an acid anhydride of formula XII in the presence of either an alkali metal salt of the corresponding acid of formula XV or an alkoxide salt of formula XIV, wherein M is an alkali metal ion and R is $C_1$ to $C_6$ alkyl; or (ii) an acid anhydride of formula XII in the presence of the corresponding acid of formula XV, preferably in the presence of a Lewis acid or strong proton acid catalyst; or (iii) with an alkali or alkaline earth metal hydride followed by reaction with an acid anhydride of formula XII or an acid halide of formula XVI; or (iv) an acid anhydride of formula XII in the presence of a strong organic base such as 4-dimethylaminopyridine or imidazole.

Alternatively, this acylation reaction may be carried out by:

(v) reacting a cyclohexane-1,3-dione derivative of formula VIII or formula IX with an acid halide of formula XVI in the presence of a base to give an intermediate O-acyl derivative of the type of formula XVII; and (vi) reacting the intermediate of formula XVII with a Lewis acid or strong proton acid catalyst; or (vii) reacting the intermediate of formula XVII with a suitable strong organic base such as 4-dimethylaminopyridine.

Part C involves the reaction of a compound of formula Xa by electrophilic aromatic nitration to give a compound of formula Xb which may readily be converted to a compound of formula Xc by reduction and N-acylation.

Part D involves the formation of a compound of the invention of formula I wherein $R^1$ is hydrogen, that is a compound of formula II. This reaction may be carried out either by reacting a 2-acyl cyclohexane-1,3-dione of formula Xc with:

(i) an alkoxyamine derivative of formula XVIII, or (ii) hydroxylamine to give an intermediate oxime derivative of formula XIX and reacting that intermediate oxime derivative of formula XIX with an alkylating agent of formula XX, wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part E involves the formation of a compound of the invention of formula I wherein $R^1$ is a substituent other than hydrogen.

Compounds of the invention of formula I, wherein $R^1$ forms an acyl derivative of a compound of formula II, may be prepared from the corresponding compounds of the invention of formula II by reacting with an acylation reagent of formula XXI, wherein L is a leaving group preferably a halogen.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:

reacting a 2-acylcyclohexane-1,3-dione derivative of formula Xc with an alkoxyamine derivative of formula XVIII to give a compound of the invention of formula II or reacting the 2-acylcyclohexane-1,3-dione derivative of formula Xc with hydroxylamine and alkylating the oxime intermediate of formula XIX with an alkylating agent of formula XX, wherein L is a leaving group, to give a compound of the invention of formula II; and optionally reacting the compound of the invention of formula II with a compound of formula XXI wherein L is a leaving group, to give a compound of the invention of formula I.

Certain of the intermediate compounds of formula Xc, are novel compounds and therefore in further embodiments the invention provides novel compounds of formula Xc, and processes for the preparation thereof.

The structures of the compounds described above are detailed on the following pages.

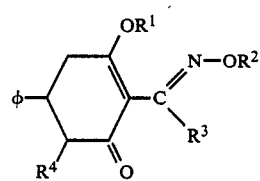  I

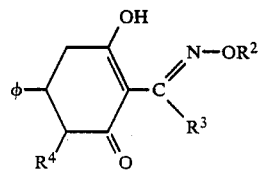  II

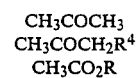

CH₃COCH₃   IVa
CH₃COCH₂R⁴   IVb
CH₃CO₂R   IVc

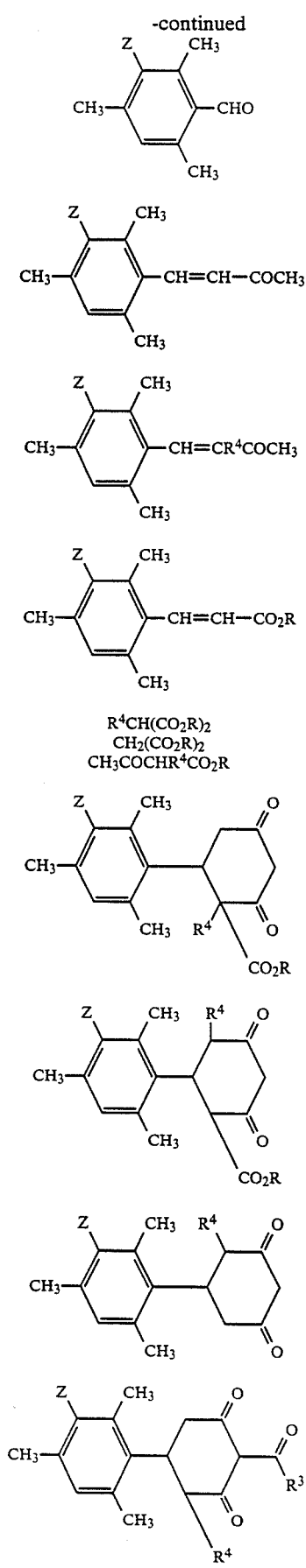
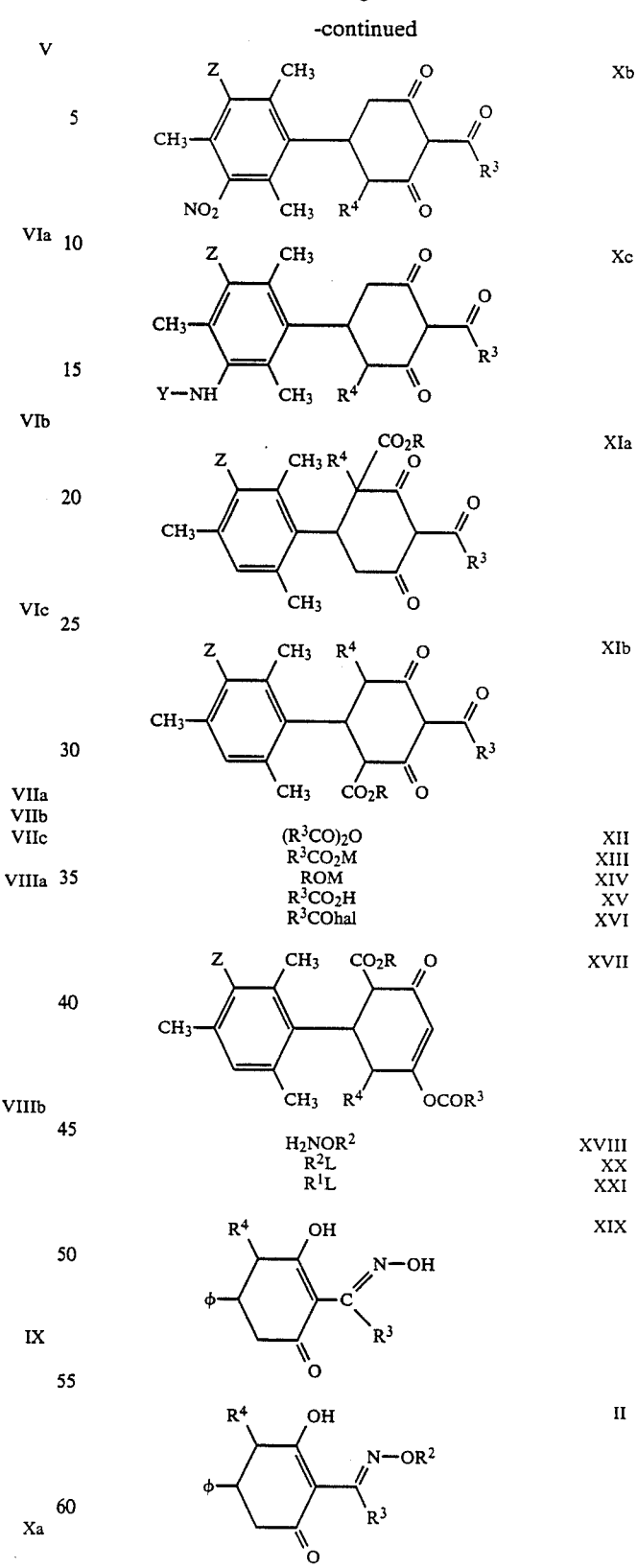
The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against monocotyledonous plants, dicotyledonous plants being relatively unaffected by rates of application of the compounds of the invention which are severely damaging or lethal to most grass species.

Accordingly, in yet a further aspect the invention provides a process for controlling monocotyledonous weeds in cultivated crops, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severly damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectivity active herbicides against wild grasses in crops of cultivated plants at some rates of application they exhibit plant growth regulating effects in said crops.

Plant growth regulating effects may be manifested in a number of ways. For example, raising the sugar content of plants, suppression of apical dominance, stimulation of auxiliary bud growth, stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley, and increasing the sugar content of sugar cane.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compostions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 10 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3,-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4-dichlorophenoxy acetic acid (common name 2,4,-D) 2,4,5-trichlorophenoxyacetic acid (common name 2,4,5-T), 4-(4-chloro-2-methylphenoxy)butyric acid (common name MCPB), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl] urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine). 2-chloro-4,6-di(ethylamino)-1,3,5-triazine (common name simazine) and 2-azido-4-(iso-propylamino)-6-methylthio-1,3,5-triazine (common name azipropytryne);

K. 1-alkoxy-2-alkyl-3-phenylurea herbicides such as 3-(3,4-dichlorophenyl)-1-methoxy-1-methylurea (common name liniuon); (3-(4-chlorophenyl)- 1-methoxy-1-methylurea (common name monolinuron) and 3-(4-bromo-4-chlorophenyl)-1-methoxy-1-methylurea (common name chlorobromuron);

L. Pyridine herbicides such as 3,6-dichloropicolinic acid (common name clopyralid) and 4-amino-3,5,6-trichloropicolinic acid (common name picloram);

M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-isopropyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichoropropionic acid and (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl --ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189);

T. Aryloxyphenoxypropionate herbicides such as butyl 2-[4-(5-trifluoromethyl-2-pyridyloxy)phenoxy]-propionate (common name fluazifop) and methyl 2-[4-(2,4-dichlorophenoxy)phenoxy]propionate (common name diclofop); and U. miscellaneous herbicides including N,N-dimethyl-diphenylacetamide (common name diphenamid), N-(1naphthyl)phthalamic acid (common name naptalam) and 3-amino-1,2,4-triazole.

Examples of useful contact herbicides include:

V. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

W. organoarsenical herbicides such as monosodium methanearsonate (common name MSMA); and X. amino acid herbicides such as N-(phosphonomethyl)glycine (common name glyphosate) and its salts and esters.

The invention is now illustrated by, but in no way limited to the following Examples.

EXAMPLE 1

2-[1-(Ethoxyimino)propyl]-3-hydroxy-5-[3-methanesulfonamido-2,4,6-trimethylphenyl]cyclohex-2-en-1-one (1)

(i) A solution of fuming nitric acid (2.17 ml), glacial acetic acid (1.98 ml) and acetic anhydride (1.94 ml) was added dropwise to a solution of 2-propionyl-3-hydroxy-5-mesitylcyclohex-2-en-1-one (10 g, 34.9 mmol) in acetic anhydride (23.3 ml) at 5°. Stirring was continued at 5° for 1 hr, then at 20° for 2 hr and 50° for 10 min. The mixture was then cooled and poured into ice water. The aqueous solution was extracted with methylene chloride. The organic layer was washed with water; saturated sodium bicarbonate solution and then further water, dried over anhydrous sodium sulfate and concentrated under reduced pressure to yield 2-propionyl-3-hydroxy-5-(3-nitro-2,4,6-trimethylphenyl)cyclohex-2-en-1-one as a pale yellow solid (9.59 g, 83%). The compound was characterized by proton magnetic resonance spectroscopy (CDCl$_3$; δ in ppm): 1.15 (3H,t), 2.18 (3H,s); 2.24 (3H,s); 2.38 (3H,s); 2.4–4.1 (7H,m); 6.88 (1H,s); 18.20 (1H,s).

(ii) Sodium dithionite (27.74 g, 159 mmol) was added over a period of 30 min to a refluxing solution of 2-propionyl-3-hydroxy-5-(3-nitro-2,4,6-trimethylphenyl)cyclohex-2-en-1-one (9.59 g, 28.9 mmol) and sodium hydroxide (1.10 g, 27.5 mmol) in 50% aqueous ethanol (350 ml). Refluxing was continued for 1 hr. The hot mixture was filtered, neutralized with dilute hydrochloric acid and extracted with methylene chloride. The organic layer was washed with water, dried over anhydrous magnesium sulfate and evaporated under reduced pressure to yield the crude 2-propionyl-3-hydroxy-5-(3-amino-2,4,6-trimethylphenyl)cyclohex-2-en-1-one as a brown oil (3.0 g, 34%). The compound was characterized by proton magnetic resonance spectroscopy (CDCl$_3$; δ in ppm): 1.17 (3H,t); 2.12 (3H,s); 2.20 (3H,s); 2.25 (3H,s); 2.3–4.2 (7H,m); 6.72 (1H,s).

(iii) Pyridine (0.53 ml, 6.6 mmol) followed by methane sulfonyl chloride (0.52 ml, 6.6 mmol) was added to a stirred solution of 2-propionyl-3-hydroxy-5-(3-amino-2,4,6-trimethylphenyl)cyclohex-2-en-1-one (1.0 g, 3.3 mmol) in methylene chloride (10 ml). Stirring was continued at 20° for 8 hr. The organic layer was washed with water, dilute hydrochloric acid and further water, dried over anhydrous magnesium sulfate and concentrated under reduced pressure to yield the crude product. The crude material was purified by column chromatography on silica gel (elution with an increasing gradient of methanol in methylene chloride) to give 2-propionyl-3-hydroxy- 5-(3-methylsulphonamido-2,4,6-trimethylphenyl)cyclohex-2-en-1-one as a yellow waxy solid (0.6 g, 50%). The compound was characterized by proton magnetic resonance spectroscopy (CDCl$_3$; δ in ppm): 1.17 (3H,t); 2.35 6H, s); 2.46 (3H,s); 3.0 (3H,s); 2.4–4.1 (7H,m); 6.78 (1H,s); 6.89 (1H,s); 18.15 (1H,brs).

(iv) Sodium acetate (0.19 g, 2.29 mmol) and ethoxyamine hydrochloride (0.22 g, 2.29 mmol) were added to a solution of 2-propionyl-3-hydroxy-5-(3-methylsulphonamido-2,4,6-trimethylphenyl)cyclohex-2-en-1-one (0.58 g, 1.53 mmol) in ethanol (25 ml) and methylene chloride (25 ml). Stirring was continued at 20° for 18 hrs. The solvent was removed under reduced pressure and the residue partitioned between chloroform and water. The organic layer was washed with water, dried over anhydrous magnesium sulfate and concentrated under reduced pressure to yield 2-[1-(ethoxyimino)-propyl]-hydroxy-5-[3-(methylsulphonamido)-2,4,6-trimethylphenyl]cyclohex-2-en-1-one as a brown oil (0.27 g, 42%). The compound was characterized by proton magnetic resonance spectroscopy. The spectroscopic data are recorded in Table 2.

EXAMPLE 2

2-[1-(Ethoxyimino)propyl]-3-hydroxy-5-(3-ethylthioureido-2,4,6-trimethylphenyl)cyclohex-2-en-1-one (3)

(i) Ethylisothiocyanate (0.35 g, 3.98 mmol) was added to a solution of 2-propionyl-3-hydroxy-5-(3-amino-2,4,6-trimethylphenyl)cyclohex-2-en-1-one (1.0 g, 3.32 mmol) in ethanol (5 ml). Stirring was continued at 20° for 4 days. Dilute acid and methylene chloride were added. The organic layer was washed with water, dried over anhydrous magnesium sulfate and concentrated. The crude product was purified by chromatography on silica gel (elution with an increasing gradient of methanol in methylene chloride) to yield 2-propionyl-3-hydroxy-5-(3-ethylthioureido-2,4,6-trimethylphenyl)-cyclohex-2-en-1-one as an oil (0.4 g, 33%). The compound was characterized by proton magnetic resonance spectroscopy (CDCl$_3$, δ in ppm): 1.12 (6H,t); 2.18 (3H,s); 2.28 (3H,s); 2.39 (3H,s); 2.4–4.2 (9H,m); 5.4 (1H,brs); 6.29 (1H,s); 8.34 (1H,brs).

(ii) 2-[1-(ethoxyimino)propyl-3-hydroxy-5-(3-ethylthioureido-2,4,6-trimethylphenyl)cyclohex-2-en-1-one was prepared from the above compound as described in Example 1, part (iv). The compound was characterized by proton magnetic resonance spectroscopy and the spectroscopic data are recorded in Table 2.

EXAMPLE 3

2-[1-(Ethoxyimino)propyl]-3-hydroxy-5-(3-ureido-2,4,6-trimethylphenyl)cyclohex-2-en-1-one (2)

(i) A solution of potassium cyanate (0.54 g, 6.66 mmol) in water (3 ml) was added cautiously to a solution of 2-propionyl-3-hydroxy-5-(3-amino-2,4,6-trimethylphenyl)cyclohex-2-en-1-one (1.0 g, 3.32 mmol) in acetic acid (9 ml) and water (3.2 ml). Stirring was continued for 1 hr then allowed to stand for 15 hr. Water and ethyl acetate were added. The organic layer was washed with water, dried over anhydrous magnesium sulfate and evaporated under reduced pressure to yield 2-propionyl-3-hydroxy-5-(3-ureido-2,4,6-trimethylphenyl)cyclohex-2-en-1-one as a brown semi solid (0.96 g, 84%). The compound was characterized by proton magnetic resonance spectroscopy (CDCl$_3$, δ in ppm): 1.11 (3H,t); 2.20 (3H,s); 2.32 (6H,s); 2.4–4.1 (7H,m); 5.12 (2H,brs); 6.82 (1H,s); 7.25 (1H,brs).

(ii) 2-[1-(Ethoxyimino)propyl]-3-hydroxy-5-(3-ureido-2,4,6-trimethylphenyl)cyclohex-2-en-1-one was prepared from the corresponding trione as described in Example 1, part (iv). The compound was characterized by proton magnetic resonance spectroscopy and the spectroscopic data are recorded in Table 2.

EXAMPLE 4

2-[1-(Ethoxyimino)propyl]-3-hydroxy-5-(3-trifluoroacetamido-2,4,6-trimethylphenyl)cyclohex-2-en-1-one (4)

(i) A solution of 2-propionyl-3-hydroxy-5-(3-amino-2,4,6-trimethylphenyl)cyclohex-2-en-1-one (0.5 g, 1.66 mmol) in trifluoroacetic anhydride (2 ml) was stirred at 20° for 48 hr. Water was then added and the aqueous layer extracted with chloroform. The organic layer was washed extensively with water, dried over sodium sulfate and concentrated under reduced pressure. The crude product was purified by column chromatography on silica gel (elution with an increasing gradient of ethylacetate in dichloromethane) to yield 2-propionyl-3-hydroxy-5-(3-trifluoroacetamido-2,4,6-trimethylphenyl)cyclohex-2-en- 1-one as a yellow solid (0.29 g, 44%). The compound was characterized by proton magnetic resonance spectroscopy (CDCl$_3$, δ in ppm): 1.16 (3H,t), 2.16 (3H,s); 2.21 (3H,s); 2.26 (3H,s); 2.4–4.1 (7H,m); 6.89 (1H,s); 8.50 (1H,s); 18.15 (1H,s).

(ii) 2-[1-(Ethoxyimino)propyl]-3-hydroxy-5-(3-trifluoroacetamido-2,4,6-trimethylphenyl)cyclohex-2-en-1-one was prepared from the above precursor as described in Example 1, part (iv). The compound was characterized by proton magnetic resonance spectroscopy and the spectroscopic data are recorded in Table 2.

EXAMPLE 5

2-[1-(Ethoxyimino)propyl]-3-hydroxy-5-[3-acetyl-5-trifluoroacetamido-2,4,6-trimethylphenyl]cyclohex-2-en-1-one (5)

(i) 2-Propionyl-3-hydroxy-5-[3-acetyl-5-nitro-2,4,6-trimethylphenyl]cyclohex-2-en-1-one was prepared from 2-propionyl-3-hydroxy-5-[3-acetyl-2,4,6-trimethylphenyl]cyclohex-2-en-1-one. The compound was characterized by proton magnetic resonance spectroscopy (CDCl$_3$, δ in ppm): 1.14 (3H,t); 2.08 (3H,s); 2.29 (6H,s); 2.46 (3H,s); 3.03 (2H,q); 2.4–4.1 (5H,m); 18.00 (1H,s).

(ii) A stirred solution of 2-propionyl-3-hydroxy-5-[3-acetyl-5-nitro-2,4,6-trimethylphenyl]cyclohex-2-en-1-one (4.2 g, 11.3 mmol) and sodium methoxide (0.61 g, 11.3 mmol) in methanol (80 ml) was hydrogenated at atmospheric pressure over 10% palladium on charcoal (0.3 g). After uptake of hydrogen ceased the solution was neutralized and the methanol was removed under reduced pressure. The residue was partitioned between water and methylene chloride. The organic layer was washed with water, dried over anhydrous sodium sulfate and evaporated under reduced pressure. The crude product was purified by chromatography on silica gel (elution with an increasing gradient of methanol in methylene chloride) to yield 2-propionyl-3-hydroxy-5-(3-acetyl-5-amino-2,4,6-trimethylphenyl)cyclohex-2-en-1-one as a red brown solid (3.28 g, 85%) the compound was characterized by proton magnetic resonance spectroscopy (CDCl$_3$, $\delta$ in ppm): 1.18 (3H,t ; 2.0 3H,s); 2.12 (3H,s); 2.18 (3H,s ; 2.40 3H,s); 2.4–4.1 (5H,m); 3.07 (2H,q); 3.6 (2H, brs); 18.05 (1H,brs).

(iii) A solution of 2-propionyl-3-hydroxy-5-(3-acetyl-5-amino-2,4,6-trimethylphenyl)cyclohex-2-en-1-one (0.46 g, 1.34 mmol) in trifluoroacetic anhydride (2 ml) was stirred at 20° for 1 hr. Water and ether were then added. The organic layer was washed extensively with water, once with saturated sodium bicarbonate solution, dried over anhydrous sodium sulfate and concentrated under reduced pressure. The crude product was purified by chromatography on silica gel (elution with 10% ethyl acetate in methylene chloride) to yield 2-propionyl-3-hydroxy-5-(3-acetyl-5-trifluoroacetamido-2,4,6-trimethyl-phenyl)cyclohex-2-en-1-one as a brown solid (0.37 g, 63%). The compound was characterized by proton magnetic resonance spectroscopy (CDCl$_3$, $\delta$ in ppm): 1.12 (3H,t, 1.73 (3H,s); 2.22 (3H,s); 2.26 (3H,s); 2.46 (3H,s); 2.4–4.1 (5H,m); 3.08 (2H,q); 9.29 1H,s); 18.33 (1H,s).

(iv) 2-[1-(Ethoxyimino)propyl]-3-hydroxy-5-[3-acetyl-5-trifluoroacetamido-2,4,6-trimethylphenyl]cyclohex-2-en-1-one was prepared from the corresponding compound detailed above as described in Example 1, part (iv). The compound was characterized by proton magnetic resonance spectroscopy. The spectroscopic data are reported in Table 2.

EXAMPLE 6

Compounds Nos 8 and 11 were prepared by a similar procedure to that described in Example 2 and starting with the appropriate isocyanate. The compounds were characterized by their behaviour on thin-layer chromatography and their proton magnetic resonance spectra. The spectroscopic data is summarized in Table 2, Example 8 below.

EXAMPLE 7

Compounds Nos 6, 7, 9 and 10 were prepared by a similar procedure to that described in Example 4 and starting with the appropriate acyl or sulfonic anhydride. The compounds were each characterized by their proton magnetic resonance spectra, together with their behaviour on thin-layer chromatography. The spectroscopic data is summarized in Table 2, Example 8 below.

EXAMPLE 8

The majority of the compounds of the invention were obtained as oils and were characterized by, and can be identified by, their nuclear magnetic resonance spectra. For convenience proton nuclear magnetic resonance (pmr) spectroscopic data is recorded in Table 2 below.

TABLE 2

| Compound No. | Appearance | Proton Chemical Shift $\delta$ in ppm (CDCl$_3$) |
|---|---|---|
| 1 | brown oil | 1.18(3H,t); 1.33(3H,t); 2.35 (6H,s); 2.44(3H,s); 3.04(3H,s); 2.4–4.2(7H,m); 4.13(2H,q); 6.85(1H,s); 6.92 (1H,s). |
| 2 | brown solid | 1.18(3H,t); 1.33(3H,t); 2.19 (3H,s); 2.35(6H,s); 2.4–4.2 (7H,m); 4.13(2H,q); 5.12(2H,brs); 6.89(1H,s); 7.3(1H,brs). |
| 3 | pale yellow solid/foam | 1.0–1.42(9H,m); 2.20(3H,s); 2.31(3H,s); 2.40(3H,s); 2.4–4.20(9H,m); 4.13(2H,q); 5.32(1H,brs); 6.98(1H,s); 8.19(1H,brs). |
| 4 | yellow oil | 1.20(3H,t); 1.27(3H,t); 2.11 (3H,s); 2.17(3H,s); 2.20(3H,s); 2.40–3.90(7H,m); 4.12 (2H,q); 7.85(1H,s); 9.85(1H,s). |
| 5 | yellow/brown solid | 1.19(3H,t); 1.34(3H,t); 1.83 (3H,s); 2.16(3H,s); 2.22(3H,s); 2.44(3H,s); 2.4–4.1(5H,m); 2.94(2H,q); 4.13(2H,q); 9.86(1H,s); 15.37(1H,brs). |
| 6 | white solid | 1.20(3H,t); 1.34(3H,t); 2.21 (3H,s); 2.29(3H,s); 2.35 (3H,s); 2.4–3.9(7H,m); 4.13 (2H,q); 6.95( 1H,s); 8.30 (1H,m), 15.0(1H,b) |
| 7 | yellow-brown solid | 1.19(3H,t); 1.34(3H,t); 2.11 (3H,s); 2.15(3H,s); 2.18 (3H,s); 2.2–3.9(7H,m); 4.12 (2H,q); 6.88(1H,s); 9.8 (1H,s); 15.2(1H,b) |
| 8 | pale brown foam | 0.82(3H,t); 1.0–1.5(8H,m); 2.18(3H,s); 2.33(6H,s); 2.3–3.9(9H,m); 4.13(2H,q); 4.6 (1H,bs); 6.6(1H,s); 6.89 (1H,s); 15.0(1H,bs) |
| 9 | pale yellow oil | 1.20(3H,t); 1.34(3H,t); 2.25(9H,bs); 2.3–3.9(7H,m); 4.12(2H,q); 6.90(1H,s); 9.1(1H,s); 15.4(1H,bs) |
| 10 | pale brown foam | 1.19(3H,t); 1.34(3H,t); 2.15 (9H,s); 2.2–3.8(7H,m); 4.12 (2H,q); 6.88(1H,s); 9.83 (1H,s); 15.4(1H,bs) |
| 11 | pale brown foam | 1.19(3H,t); 1.33(3H,t); 2.18 (3H,s); 2.31(3H,s); 2.36 (3H,s); 2.3–4.0(7H,m); 2.72(3H,d); 4.13(2H,q); 4.5(1H,bs); 6.62(1H,s); 6.90(1H,s); 15.0 (1H,b) |

EXAMPLE 9

This non-limiting Example illustrates the preparation of formulations of the compounds of the invention.

(a) Emulsifiable Concentrate

Compound No 2 was dissolved in toluene containing v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 8 (5 parts by weight and "Dyapol" PT (1 part by weight) were added to a 2% aqueous solution (94 parts by weight) of "Teric" N8 and the mixture was ball milled to produce a stable aqueous suspension which may be diluted with water to the required concentration to give an aqueous suspension which may be diluted with water to the required concentration to give an aqueous suspension which may be applied by spraying.

("Dyapol" is a Trade mark and "Dyapol" PT is an anionic suspending agent; "Teric" N8 is a product of ethoxylation of nonylphenol.)

(c) Emulsifiable Concentrate

Compound No 2 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 1 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns.

("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) Dusting Powder

Compound No 1 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part a), b) or c) above and then diluted with water, optionally containing surface active agent and/or oil, to give aqueous compositions of the required concentration which were used, as described in Examples 10 to 12, in the evaluation of the pre-emergence and post-emergence herbicidal activity of the compounds.

EXAMPLE 10

The pre-emergent herbicidal activity of the compounds of the invention formulated as described in Example 9 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
B: Barley
P: Peas
IP: Ipomea
Ms: Mustard
Sf: Sunflower

TABLE 3

Pre-emergent Herbicidal Activity

| Compound No. | Application Rate kg/ha | Wh | Jm | Rg | Ot | B | P | Ip | Ms | Sf |
|---|---|---|---|---|---|---|---|---|---|---|
| 1 | 1.0 | 2 | 5 | 5 | 3 | 5 | 0 | 0 | 0 | 0 |
| 2 | 1.0 | 3 | 5 | 4 | 3 | 2 | 0 | 0 | 0 | 0 |
| 3 | 1.0 | 5 | 5 | 5 | 5 | 5 | 0 | 0 | 0 | 0 |
| 3 | 0.25 | 4 | 5 | 4 | 4 | 2 | — | — | — | — |
| 4 | 1.0 | 5 | 5 | 5 | 5 | 5 | 0 | 0 | 0 | 0 |
| 4 | 0.25 | 5 | 5 | 5 | 5 | 5 | — | — | — | — |
| 5 | 1.0 | 5 | 5 | 5 | 5 | 5 | 0 | 0 | 0 | 0 |
| 5 | 0.25 | 5 | 5 | 5 | 5 | 5 | — | — | — | — |
| 6 | 1.0 | 5 | 5 | 5 | 5 | 4 | 0 | 5 | 5 | 4 |
| 7 | 1.0 | 2 | 5 | 5 | 5 | 1 | 0 | 0 | 0 | 0 |
| 8 | 1.0 | 5 | 5 | 5 | 5 | 5 | 1 | 0 | 1 | 1 |
| 8 | 0.25 | 5 | 5 | 5 | 5 | 5 | — | — | — | — |
| 9 | 1.0 | 5 | 5 | 5 | — | 5 | 4 | 2 | 0 | 1 |
| 9 | 0.25 | 3 | 5 | 5 | — | 5 | — | — | — | — |
| 10 | 1.0 | 5 | 5 | 5 | 5 | 5 | 0 | 0 | 0 | 0 |
| 10 | 0.25 | 5 | 4 | 5 | 5 | 5 | — | — | — | — |
| 11 | 1.0 | 5 | 5 | 5 | 5 | 5 | 0 | 0 | 0 | 0 |
| 11 | 0.25 | 5 | 5 | 5 | 5 | 5 | — | — | — | — |

EXAMPLE 11

The post-emergent herbicidal activity of the compounds of the invention formulated as described in Example 9 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
B: Barley
P: Peas
Ip: Ipomea Ms: Mustard
Sf: Sunflower

TABLE 4

| Compound No. | Application Rate kg/ha | Wh | Jm | Rg | Ot | B | P | Ip | Ms | Sf |
|---|---|---|---|---|---|---|---|---|---|---|
| 1 | 0.25 | 5 | 5 | 5 | 5 | 5 | — | — | — | — |
|   | 0.0625 | 3 | 5 | 4 | 5 | 4 | — | — | — | — |
| 2 | 1.0 | 5 | 5 | 5 | 5 | 5 | 0 | 0 | 0 | 0 |
|   | 0.25 | 4 | 5 | 5 | 5 | 4 | — | — | — | — |
| 3 | 1.0 | 5 | 5 | 5 | 5 | 5 | 0 | 0 | 0 | 0 |
|   | 0.25 | 4 | 5 | 5 | 5 | 5 | — | — | — | — |
|   | 0.0625 | 4 | 5 | 4 | 5 | 5 | — | — | — | — |
| 4 | 1.0 | 5 | 5 | 5 | 5 | 5 | 0 | 0 | 0 | 0 |
|   | 0.25 | 5 | 5 | 5 | 5 | 5 | — | — | — | — |
|   | 0.0625 | 5 | 5 | 5 | 5 | 5 | — | — | — | — |
| 5 | 1.0 | 5 | 5 | 5 | 5 | 5 | 0 | 3 | 3 | 2 |
|   | 0.25 | 5 | 5 | 5 | 5 | 5 | — | — | — | — |
|   | 0.0625 | 5 | 5 | 5 | 5 | 5 | — | — | — | — |
| 6 | 1.0 | 5 | 5 | 5 | 5 | 5 | 0 | 0 | 0 | 0 |
|   | 0.25 | 2 | 5 | 4 | 4 | 5 | — | — | — | — |
|   | 0.0625 | 3 | 5 | 3 | 4 | 5 | — | — | — | — |
| 7 | 1.0 | 4 | 5 | 5 | 5 | 4 | 0 | 0 | 0 | — |
| 8 | 1.0 | 5 | 5 | 5 | 5 | 5 | 5 | 0 | 1 | 3 |
|   | 0.25 | 5 | 5 | 5 | 5 | 5 | — | — | — | — |
|   | 0.0625 | 5 | 5 | 5 | 5 | 5 | — | — | — | — |
| 9 | 1.0 | 5 | 5 | 5 | 5 | 5 | 3 | 3 | 4 | 2 |
|   | 0.25 | 5 | 5 | 5 | 5 | 5 | — | — | — | — |
|   | 0.0625 | 5 | 5 | 5 | 5 | 5 | — | — | — | — |
| 10 | 1.0 | 5 | 5 | 5 | 5 | 5 | 0 | 0 | — | 0 |
|    | 0.25 | 5 | 5 | 5 | 5 | 5 | — | — | — | — |
| 11 | 1.0 | 5 | 5 | 5 | 5 | 5 | 0 | 0 | — | 2 |
|    | 0.25 | 5 | 5 | 5 | 5 | 5 | — | — | — | — |

EXAMPLE 12

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 5 below. Damage to test plants was assessed after 14 days on a scale of 0 to 5 where 0 is 0 to 20% damage and 5 is complete kill. The degree of herbicidal damage was assessed by comparison with untreated control plants. The results are given in Table 5 below. A dash (-) means that no experiment was carried out.

The names of the test plants were as follows:
Mz: Maize
Ww: Winter wheat
Rc: Rice
Br: Barley
Av: *Avena fatua*
Dg: *Digitaria sanguinalis*
Al: *Alopecurus myosuroides*
St: *Setaria viridis*
Ec: *Echinochloa crus-galli*
Sh: *Sorghum halepense*
Ag: *Agropyron repens*

TABLE 5

| Compound No. | Application Rate (Kg/ha) | Mz | Ww | Rc | Br | Av | Dg | Al | St | Ec | Sh | Ag |
|---|---|---|---|---|---|---|---|---|---|---|---|---|
| 1 | 0.2 | 4 | — | — | 4 | 5 | 4 | 4 | 4 | 4 | 4 | — |
| 1 | 0.1 | 3 | — | — | 4 | 4 | 4 | 4 | 4 | 4 | 3 | — |
| 1 | 0.25 | 4 | 2 | 0 | 4 | 4 | 4 | 4 | 4 | 4 | 3 | 2 |
| 2 | 0.2 | 5 | 4 | 4 | 4 | 4 | 4 | 4 | 5 | 4 | 4 | 4 |
| 2 | 0.1 | 4 | 4 | 4 | 3 | 4 | 4 | 4 | 5 | 3 | 3 | 3 |
| 3 | 0.2 | 5 | 4 | 4 | 4 | 4 | 4 | 5 | 4 | 5 | 4 | 4 |
| 3 | 0.1 | 4 | 4 | 2 | 4 | 4 | 3 | 4 | 3 | 5 | 3 | 3 |
| 4 | 0.2 | 4 | 3 | 3 | 5 | 5 | 4 | 4 | 2 | 5 | 4 | 4 |
| 4 | 0.1 | 3 | 1 | 1 | 4 | 5 | 3 | 4 | 2 | 5 | 4 | 3 |
| 4 | 0.05 | 0 | 1 | 0 | 4 | 4 | 3 | 3 | 1 | 4 | 0 | 0 |
| 5 | 0.2 | 5 | 4 | 4 | 5 | 5 | 5 | 5 | 5 | 5 | 5 | 5 |
| 5 | 0.05 | 5 | 4 | 1 | 4 | 5 | 4 | 5 | 5 | 5 | 4 | 4 |
| 6 | 0.2 | 4 | 4 | 4 | 4 | 5 | 4 | 4 | 4 | 5 | 4 | 4 |
| 6 | 0.1 | 4 | 4 | 3 | 4 | 5 | 3 | 4 | 4 | 5 | 4 | 3 |
| 7 | 0.2 | 4 | 3 | 3 | 4 | 4 | 4 | 4 | 3 | 4 | 3 | 1 |
| 8 | 0.12 | 4 | 4 | 3 | 4 | 5 | 5 | 5 | 5 | 5 | 5 | 4 |
| 8 | 0.02 | — | — | — | — | 4 | 5 | 4 | 3 | 5 | 2 | 2 |
| 10 | 0.1 | 0 | 2 | 1 | 2 | 4 | 4 | 4 | 3 | 4 | 2 | 0 |
| 11 | 0.15 | 5 | 4 | 3 | 5 | 5 | 5 | 5 | 4 | 5 | 4 | 4 |
| 11 | 0.05 | 2 | 4 | 2 | 4 | 5 | 4 | 4 | 4 | 5 | 2 | 3 |

We claim:
1. A compound of formula I

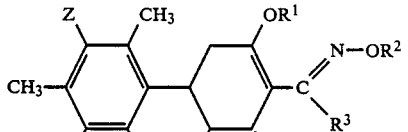

wherein
Y is selected from the group consisting of:
$C_1$ to $C_6$ alkylsulfonyl; $C_1$ to $C_6$ haloalkylsulfonyl; $C_2$ to $C_6$ haloalkanoyl; $R^5CO$ and $R^5CS$ wherein $R^5$ is selected from the group consisting of: hydroxy, $C_1$ to $C_6$ alkoxy, amino, $C_1$ to $C_6$ alkylamino and di($C_1$ to $C_6$ alkyl)amino;
Z is selected from the group consisting of hydrogen, halogen, $C_1$ to $C_4$ alkyl, $C_2$ to $C_4$ alkanoyl, sulfamoyl, $C_1$ to $C_4$ alkylsulfamoyl, di($C_1$ to $C_4$ alkyl)sulfamoyl, carboxy and trifluoroacetylamino;
$R^1$ is selected from the group consisting of: hydrogen; $C_2$ to $C_6$ alkanoyl and the alkali metal cations;

$R^2$ is selected from the group consisting of: to $C_6$ alkyl; $C_1$ to $C_6$ haloalkyl; $C_2$ to $C_6$ alkenyl; $C_2$ to $C_6$ haloalkenyl and $C_3$ to $C_6$ alkynyl;

$R^3$ is selected from the group consisting of: $C_1$ to $C_6$ alkyl; and $R^4$ is selected from the group consisting of: hydrogen; $C_1$ to $C_6$ alkyl; and ($C_1$ to $C_6$ alkoxy) carbonyl.

2. A compound according to claim 1 wherein:

Y is selected from the group consisting of:

$C_1$ to $C_6$ alkylsulfonyl; $C_1$ to $C_6$ haloalkylsulfonyl; $C_2$ to $C_6$ haloalkanoyl; aminocarbonyl; $C_1$ to $C_6$ alkoxythiocarbonyl; amino thiocarbonyl; $C_1$ to $C_6$ alkyl aminothiocarbonyl, and di($C_1$ to $C_6$ alkyl) aminothiocarbonyl.

3. A compound according to claim 1 wherein:

Y is selected from the group consisting of:

$C_1$ to $C_6$ alkylsulfonyl; $C_1$ to $C_6$ haloalkylsulfonyl; $C_2$ to $C_6$ haloalkanoyl; $R^5CO$ and $R^5CS$ wherein $R^5$ is selected from amino, $C_1$ to $C_6$ alkylamino and di($C_1$ to $C_6$ alkyl) amino;

Z is selected from the group consisting of: hydrogen, halogen, $C_1$ to $C_4$ alkyl and $C_2$ to $C_4$ alkanoyl;

$R^1$ is selected from the group consisting of: hydrogen; $C_2$ to $C_6$ alkanoyl and the alkali metal cations;

$R^2$ is selected from the group consisting of: $C_1$ to $C_6$ alkyl; $C_2$ to $C_6$ alkenyl and $C_3$ to $C_6$ alkynyl;

$R^3$ is selected from the group consisting of: $C_1$ to $C_6$ alkyl;

$R^4$ is hydrogen

4. A compound according to claim 3 wherein:

Y is selected from the group consisting of:

$C_1$ to $C_4$ haloalkylsulfonyl; $C_2$ to $C_4$ haloalkanoyl; carbamoyl; thiocarbamoyl; $C_1$ to $C_4$ alkylcarbamoyl; $C_1$ to $C_4$ alkylthiocarbamoyl;

Z is selected from the group consisting of: hydrogen, halogen, methyl and $C_2$ to $C_4$ alkanoyl;

$R^1$ is selected from hydrogen and the alkali metal cations;

$R^2$ is selected from $C_1$ to $C_4$ alkyl; $C_2$ to $C_4$ alkenyl and $C_3$ to $C_4$ alkynyl;

$R^3$ is selected from $C_1$ to $C_4$ alkyl;

$R^4$ is hydrogen.

5. A compound according to claim 5 wherein:

Y is selected form the group consisting of:

trifluoromethanesulfonyl, trifluoroacetyl, trichloroacetyl, carbamoyl, ethylthiocarbamoyl, methylcarbamoyl and propylcarbamoyl;

Z is hydrogen or acetyl;

$R^1$ is hydrogen;

$R^2$ is selected from ethyl, allyl and propargyl;

$R^3$ is methyl, ethyl or propyl;

$R^4$ is hydrogen.

6. A compound according to claim 6 selected from the group consisting of:

2-[1-(Ethoxyimino)propyl]-3-hydroxy-5-(2,4,6-trimethyl-3-trifluoroacetylaminophenyl)cyclohex-2-en-1-one;

2-[1-(Ethoxyimino)propyl]-3-hydroxy-5-(3-acetyl-2,4,6-trimethyl-5-trifluoroacetylaminophenyl)cyclohex-2-en-1-one;

2-[1-(Ethoxyimino)propyl]-3-hydroxy-5-[3-(N'-methylureido)-2,4,6-trimethylphenyl]cyclohex-2-en-1-one;

2-[1-(Ethoxyimino)propyl]-3-hydroxy-5-[3-(N'-n-propylureido)-2,4,6-trimethylphenyl]cyclohex-2-en-1-one.

7. A herbicidal composition comprising as active ingredient a compound as defined according to claim 1 and a carrier therefor.

8. A process for severely damaging or killing unwanted plants which process comprises applying to said plants, or to the growth medium of said plants, an effective amount of a compound as defined according to claim 1.

9. A process for selectively controlling the growth of monocotyledonous weeds in dicotyledonous crops which process comprises applying to said crop, or to the growth medium of said crop, a compound as defined according to claim 1 in an amount sufficient to severely damage or kill said weeds but insufficient to substantially damage said crop.

10. A process according to or claim 9 wherein the compound is applied at a rate in the range of from 0.005 to 20 kilograms per hectare.

* * * * *